(12) United States Patent
Li et al.

(10) Patent No.: US 7,801,687 B1
(45) Date of Patent: *Sep. 21, 2010

(54) CHEMICAL SENSORS USING COATED OR DOPED CARBON NANOTUBE NETWORKS

(75) Inventors: Jing Li, San Jose, CA (US); Meyya Meyyappan, San Jose, CA (US)

(73) Assignee: The United States of America as represented by the Administrator of the National Aeronautics and Space Administration (NASA), Washington, DC (US)

( * ) Notice: Subject to any disclaimer, the term of this patent is extended or adjusted under 35 U.S.C. 154(b) by 938 days.

This patent is subject to a terminal disclaimer.

(21) Appl. No.: 11/178,079

(22) Filed: Jul. 8, 2005

(51) Int. Cl.
*G01N 31/00* (2006.01)
(52) U.S. Cl. .............. 702/22; 702/23; 702/24; 702/27; 702/30; 702/32; 422/83; 422/98; 436/149; 73/23.2; 73/23.21; 977/920; 977/921; 977/922; 977/938
(58) Field of Classification Search .................. 73/23.2; 436/150, 153; 702/27
See application file for complete search history.

(56) References Cited

U.S. PATENT DOCUMENTS

| | | | |
|---|---|---|---|
| 6,289,328 | B2 | 9/2001 | Shaffer |
| 6,528,020 | B1 * | 3/2003 | Dai et al. ............... 422/98 |
| 6,537,498 | B1 | 3/2003 | Lewis et al. |
| 7,312,095 | B1 | 12/2007 | Gabriel et al. |
| 7,318,908 | B1 | 1/2008 | Dai |
| 2003/0175161 | A1 * | 9/2003 | Gabriel et al. ........... 422/90 |
| 2005/0126913 | A1 * | 6/2005 | Burke et al. ............. 204/547 |
| 2005/0169798 | A1 | 8/2005 | Bradley et al. |

OTHER PUBLICATIONS

Cinke, et al, Pore structure of raw and purified HiPco single-walled carbon nanotubes, Chemical Physics Letters, 2002, 69-74, 365, Elsevier Science B.V., www.sciencedirect.com.

(Continued)

*Primary Examiner*—Tony G Soohoo
*Assistant Examiner*—Robert Eom
(74) *Attorney, Agent, or Firm*—John Schippar; Robert Padilla; Diana Cox (57) ABSTRACT

Methods for using modified single wall carbon nanotubes ("SWCNTs") to detect presence and/or concentration of a gas component, such as a halogen (e.g., $Cl_2$), hydrogen halides (e.g., HCl), a hydrocarbon (e.g., $C_nH_{2n+2}$), an alcohol, an aldehyde or a ketone, to which an unmodified SWCNT is substantially non-reactive. In a first embodiment, a connected network of SWCNTs is coated with a selected polymer, such as chlorosulfonated polyethylene, hydroxypropyl cellulose, polystyrene and/or polyvinylalcohol, and change in an electrical parameter or response value (e.g., conductance, current, voltage difference or resistance) of the coated versus uncoated SWCNT networks is analyzed. In a second embodiment, the network is doped with a transition element, such as Pd, Pt, Rh, Ir, Ru, Os and/or Au, and change in an electrical parameter value is again analyzed. The parameter change value depends monotonically, not necessarily linearly, upon concentration of the gas component. Two general algorithms are presented for estimating concentration value(s), or upper or lower concentration bounds on such values, from measured differences of response values.

12 Claims, 9 Drawing Sheets

OTHER PUBLICATIONS

Kong, et al., Nanotube Molecular Wires as Chemical Sensors, Science, Jan. 28, 2000, 622-625, 287, Science, www.sciencemag.org.

Li, The Cyranose Chemical Vapor Analyzer, Sensors, Aug. 2000, 1-9.

Li, Carbon Nanotube Applications: Chemical and Physical Sensors, Carbon Nanotubes: Science & Applications, 2004, 213-233, CRC Press LLC, Boca Raton, Florida.

Li, et al., Carbon Nanotube Sensors for Gas and Organic Vapor Detection, Nano Letters, 2003, 929-933, 3-7.

Matthews, et al., Effects of Electrode Configuration on Polymer Carbon-Black Composite Chemical Vapor Sensor Performance, IEEE Sensors Journal, Jun. 2002, 160-168, 2-3, IEEE.

Lu, et al., Room temperature methane detection using palladium loaded single-walled carbon nanotube sensors, Chemical Physics Letters, 2004, 344-348, 391, Elsevier B.V.

Young, et al., High-Sensitivity NO2 Detection with Carbon Nanotube—Gold Nano . . . , J. Nanoscience and Nanotechnology, 2005, 1509-1513, 5, American Scientific Publishers, USA.

Janata, Principles of Chemical Sensors, 1989, pp. 175-239, Plenum Press, New York.

Response to first office action for related NASA, U.S. Appl. No. 11/591,630, filed Oct. 31, 2006, 8 pages.

First Office Action in related case, mailing date May 29, 2009, U.S. Appl. No. 11/489,803, filed Jul. 12, 2006.

Calusdian, et al., Design and Testing of a Wireless Portable Carbon Nanotube-Based Chemical Sensor System, Sixth IEEE Conference on Nanotechnology, Jun. 17-20, 2006, 794-797.

First Office Action in related case, mailed Sep. 4, 2009, U.S. Appl. No. 11/416,505, filed Apr. 28, 2006.

Shaffer, et al., A comparison study of chemical sensor array pattern recognition algorithms, Analytica Chimica Acta 384, 1999, 305-317, Elsevier.

Response to Nonfinal Rejection in related case, mailed May 29, 2009, U.S. Appl. No. 11/489,803, filed Jul. 12, 2006.

Response to nonfinal rejection, mailed Mar. 12, 2008, in related case, U.S. Appl. No. 11/591,630, Response filed Sep. 10, 2008.

Response to nonfinal rejection, mailed Sep. 4, 2009, in related case, U.S. Appl. No. 11/416,505, Response filed Mar. 4, 2010.

Final Rejection in related case, mailed Jun. 24, 2010, U.S. Appl. No. 11/416,505, filed Apr. 28, 2010.

* cited by examiner 12A, 12B,
13A  13B

CHEMICAL SENSORS USING COATED OR DOPED CARBON NANOTUBE NETWORKS

ORIGIN OF THE INVENTION

This invention was made, in part, by one or more employees of the U.S. government. The U.S. government has the right to make, use and/or sell the invention described herein without payment of compensation therefor, including but not limited to payment of royalties.

FIELD OF THE INVENTION

This invention relates to use of carbon nanotube networks as sensors of chemical substances.

BACKGROUND OF THE INVENTION

Chemical sensors have been developed for decades now to detect gases and vapors at various concentration levels for deployment in a wide range of industrial applications. The detection usually centers on a change of a particular property or status of the sensing material (such as temperature, electrical, optical characteristics, etc.) upon exposure to the chemical species of interest. The selection of sensing material itself has spanned across the periodic table with a range of inorganic, semiconducting elements and organic compounds either in bulk or thin film form. Perhaps the most widely investigated class of sensors is the high temperature metal oxide sensor due to its high sensitivity with tin oxide as an example of sensor material. The most common $SnO_2$ sensor platform has been a chemiresistor wherein the transport characteristics of a conducting channel of tin oxide is modulated by the adsorption of chemical species at elevated temperatures ($T \geq 350°$ C.). Other types of sensors include electrochemical cells, conducting polymer sensors, surface acoustic wave sensors and catalytic bead sensors.

While commercial sensors based on some of the above approaches are available, research continues on new sensing materials and transducer platforms for improved performance. Desirable attributes of next generation sensors include high sensitivity in the parts per million (ppm) to parts per billion (ppb) range, low power consumption, room temperature operation, rapid response time, and high selectivity and long term stability. Sensors based on the emerging nanotechnology promise to provide improved performance on all of the above metrics compared to the current micro and macro sensors. Nanomaterials exhibit small size, light weight, very high surface to volume ratio, increased chemical reactivity compared to bulk materials, and mechanically stable so that a sensing material can be refreshed or regenerated many times. All these properties are ideal for developing extremely sensitive chemical sensors.

Among the numerous nanomaterials, carbon nanotubes (CNTs) have received significant attention due to their unique electronic and extraordinary mechanical properties. Single-wall carbon nanotubes (SWCNTs) have an enormous surface area, as high as about 1600 $m^2$/gm, which leads to an increased adsorptive capacity for gases and vapors. With all the atoms on the surface, SWCNTs are expected to exhibit a change in properties sensitively upon exposure to the environment. Indeed, electrical conductivity of SWCNTs has been shown to change reproducibly in the presence of gases such as $NO_2$ and $NH_3$. This revelation has resulted in the fabrication of SWCNT-based chemical sensors by several groups.

The principal platform for such sensors has been nanotube field effect transistor ("CNT-FET") with a single SWCNT serving as the conducting channel. This platform faces some serious difficulties for commercialization. First, the CNT-FET requires semiconducting SWCNTs for its operation, and selective growth of metallic versus semiconducting nanotubes is not possible today. Second, if an in situ chemical vapor deposition ("CVD") process is used in the device fabrication sequence, it is hard to make a single SWCNT grow horizontally in order to bridge a given distance between the source and the drain. Alternatively, one is forced to 'pick and place' a semiconducting SWNT from bulk samples. Finally, the chemical sensor market is too cost sensitive to rely on complex steps involved in CNT-FET fabrication resulting in low sensor yield and poor reproducibility.

What is needed is an approach using suitably modified nanomaterials, such as SWCNTs, that can detect presence of certain gas components whose presence cannot be detected by any simple means. Preferably, the method should provide high sensitivity (detection of parts per million or parts per billion of the target gas), high selectivity, room temperature operation, low power consumption, high throughput and low cost. Preferably, the method(s) should extend to detection of other gas components with at most modest changes in the nanomaterial modification procedures.

SUMMARY OF THE INVENTION

These needs are met by the invention, which provides a chemical sensor or sensor array for detecting presence, at or near room temperature, of one or more of N target gas components or molecules ($N \geq 1$) in a gas mixture contained in a chamber, by any ambient being considered. The sensor contains a network of SWCNTs that is connected to a controllably variable voltage difference or current source. The chamber may be closed, isolated and static; or, preferably, may allow gas flow-through and thus not be wholly isolated from the external environment. Alternatively, the chamber may be part or all of the external environment.

In a first embodiment, the SWCNTs in the network are partly or wholly coated with a selected polymer, such as chlorosulfonated polyethylene, hydroxypropyl, polystyrene or polyvinylalcohol, and the target molecule may be a hydrocarbon $C_mH_n$, (e.g., $CH_4$ or $C_3H_7$ or $C_2H_2$), an alcohol $C_mH_n$, OH, a ketone (e.g., $CH_3(CO)CH_3$) or an aldehyde (e.g., $C_2H_5$ (COH). An algorithm, applicable to any embodiment, provides an estimate of target molecule concentration.

In a second embodiment, the SWCNTs in the network are doped with a selected transition element, such as Pd, Pt, Rh, Ir, Ru, Os and/or Au. In either embodiment, a value of an electrical parameter, such as conductivity, resistivity, electrical current or voltage difference, is measured and compared with the parameter value for the network with no coating and no doping. SWCNTs are positioned between the electrodes using either a solution casting process in the form of a network or in situ growth using chemical vapor deposition (CVD) techniques. Polymer coating or transition element doping of SWCNTs allows selective sensing of certain gases, as demonstrated here for chlorine ($Cl_2$), HCl, $CH_4$ and $CO_x$ vapor. The CNT sensors may be formed on a substrate, such as silicon, ceramic, glass and selected polymers. The sensor fabrication process is scalable for manufacturing products that include wafer scale IDE fabrication and inkjet deposition of SWCNTs and polymers for coatings and metal nanoparticles for doping.

DESCRIPTION OF BEST MODES OF THE INVENTION

Figure 1A:
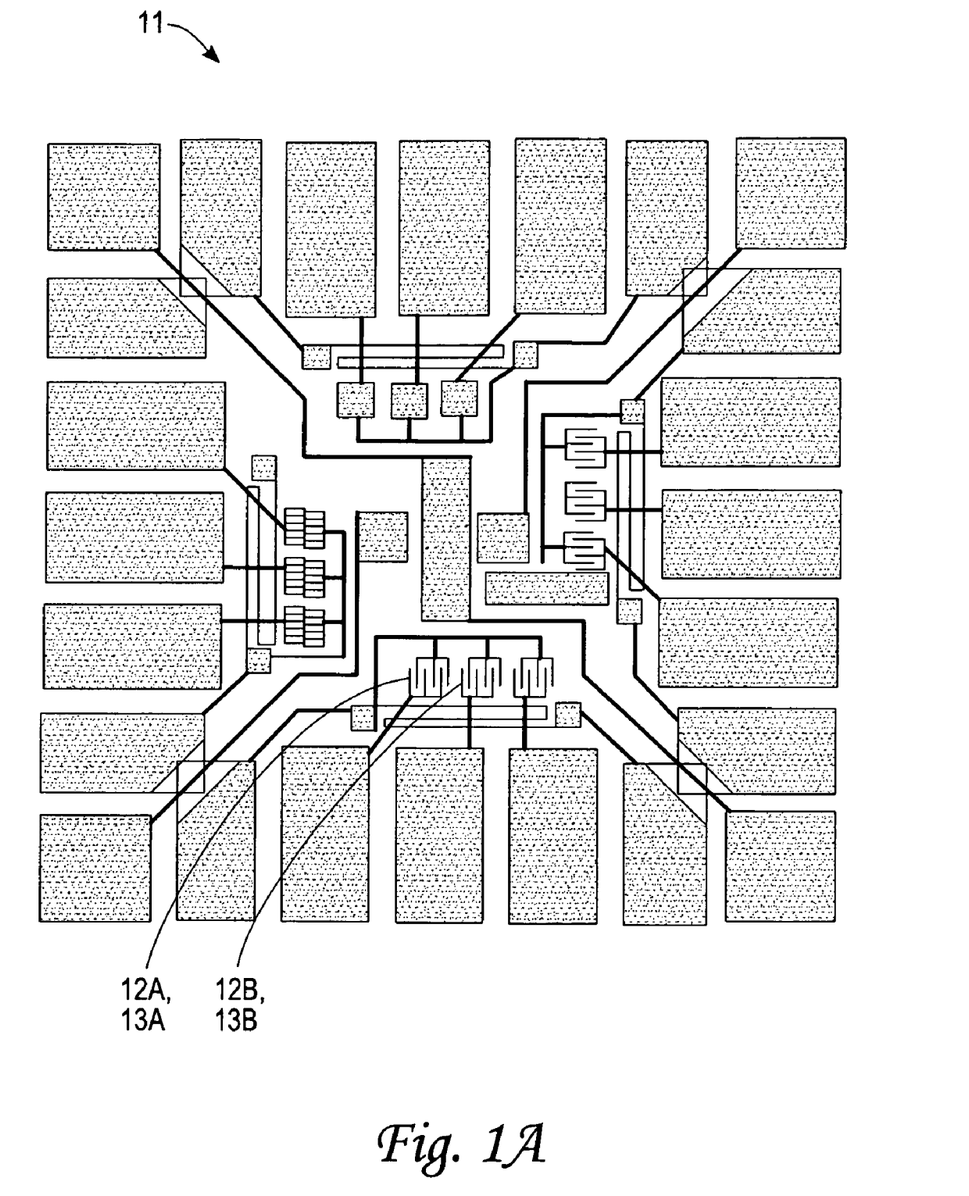
FIGS. 1A and 1B illustrate use of a network of SWCNTs to connect two electrodes according to the invention.
Figure 1B:
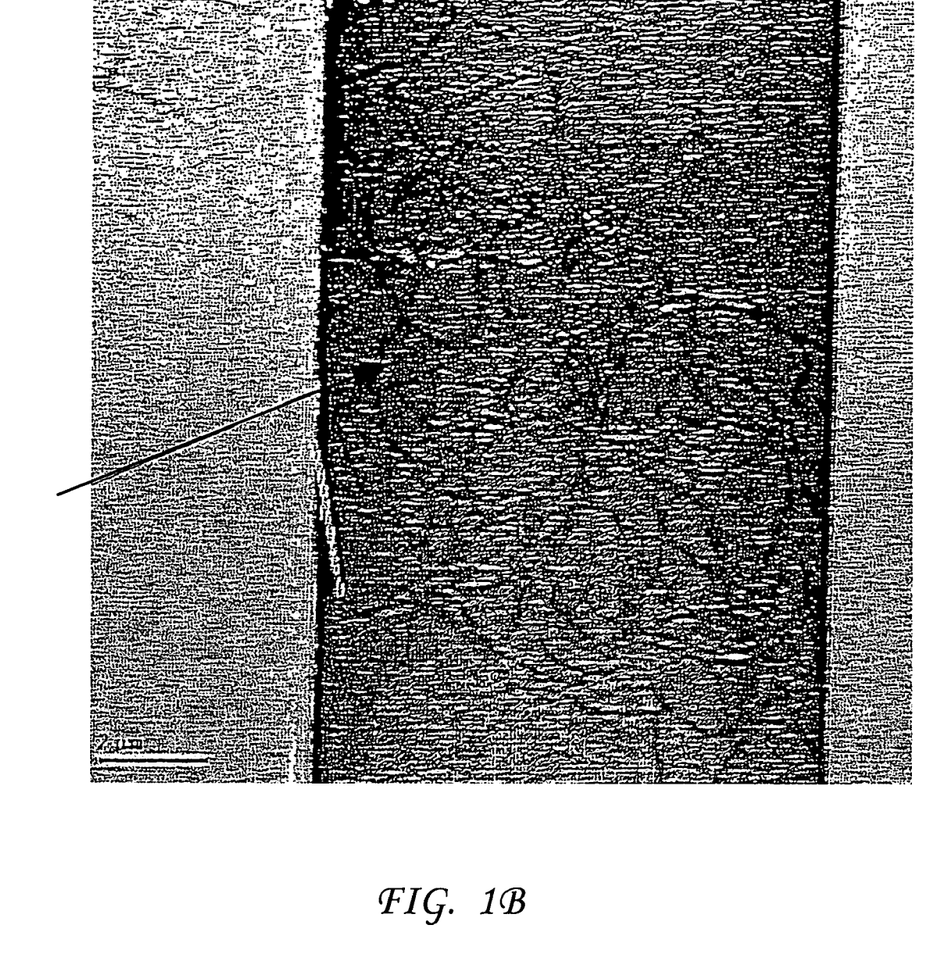

FIGS. 1A and 1B illustrate a sensor 11, constructed according to the invention, including interdigitated electrode fingers ("IDEFs"), 12A and 12B, with corresponding fingers, connected to respective first and second voltage sources, 13A and 13B, with a controllable voltage difference. In FIG. 1A, a 1 cm×1 cm chip with Q sensing elements and SWCNTs bridging the gaps between adjacent IDEFs (herem Q=2-12). Each IDE was fabricated using conventional photolithography with a nominal finger width of 10 µm and gap sizes of 4, 8, 12 and 50 µm, or any other desired set of gap sizes. The fingers and contact pads, 11A-i and 11B-j, were thermally evaporated Ti (20 nm thickness) and Pt (200 nm thickness) on a layer of $SiO_2$, thermally grown on a silicon substrate. The sensing material was bulk-produced SWCNTs from a HiPCo process (Rice University.), purified to remove amorphous carbon and metal impurities according to a procedure described in the literature. The purified SWCNTs were dispersed in a selected solvent, such as dimethyl formamide, to create a suspension of SWCNTs. The suspension was sonicated and then drop-deposited onto the interdigitated area of the electrodes. After the solvent evaporated, the SWCNTs formed a network connecting two adjacent fingers with a corresponding voltage difference. Any residue of the solvent was thoroughly removed by drying the sensor under vacuum. The SWCNT density in the network can be varied by varying the amount of suspension or the concentration of SWCNTs in the suspension placed on the sensor area. This process produces a statistically meaningful number of SWCNTs bridging the gap between two terminals to give reproducible performance. Alternatively, the SWCNTs can be grown directly on the electrodes using chemical vapor deposition. A selected electrical parameter response value, such as conductance or resistivity or electrical current or voltage difference, is provided or measured for the uncoated and modified SWCNT networks. Differences between the sensing elements are compensated for by varying a base resistance located in series with each sensing element.

SWCNTs yield different signal response when exposed to different gases and vapors and one must use pattern recognition or intelligent signal processing techniques for the identification of the gas constituent of interest. SWCNTs do not respond to exposure to certain gases and vapors, and in those cases, coating or doping of the nanotubes may elicit a signal. Chlorosulfonated polyethylene, having a mass of 0.804 mg, was dissolved in a solvent of 25 ml tetrafluoro furan (THF) as a coating for sensing presence of $Cl_2$. Hydroxypropyl cellulose, having a mass of 0.791 gm, was dissolved in a solvent of 25 ml chloroform for coating the nanotubes to detect presence of HCl. In each case, an aliquot of 5 nl polymer solution was drop-deposited onto the SWCNT network in FIG. 1A to coat the corresponding SWCNTs.

The electrical current through the sensors, at a constant voltage of 1 Volt, was monitored as different concentrations of chlorine ($Cl_2$) and of hydrochloric acid (HCl) vapor were introduced to the sensor's environment sequentially. A voltage difference of even less than 1 Volt (or greated, if desired) can be used here because the electrical conductivity of CNTs is so large. A computerized gas blending and dilution system, Environics 2040 (Environics, Inc. Tolland, Conn.), was used to create different concentration streams with a steady flow of 400 cc/min during both exposure and purge periods. A gas cylinder containing 98.3 ppm $Cl_2$ gas balanced with nitrogen, and a gas cylinder containing 478 ppm HCl with nitrogen, were used as the source gases. Nitrogen was used both as the purge gas and as the balance gas for creating low concentration test samples. The test sample concentrations were 1, 2 and 5 ppm for $Cl_2$ gas and 5, 10 and 40 ppm for HCl gas. The electrical signal (current) was collected using a semiconductor parameter analyzer HP4155B (Agilent, Palo Alto, Calif.). Other equivalent electrical parameters, such as conductance or resistance, can be used as a response value. In trials involving heating, a thermal controller, Micro-Infinity ICN77000 Series Controller (Newport Electronics, Inc., Santa Ana, Calif.) with a thermocouple, maintained a constant temperature for the sensor operation. Additionally, a vacuum pump and an ultraviolet lamp of wavelength 254 nm were employed on occasion to accelerate the recovery of the sensors between tests; other ultraviolet wavelengths, such as 300 nm and 360 nm, can also be used to accelerate recovery.

Carbon nanotubes do not sense presence of some gases and vapors due to the chemical and physical properties of CNTs as well as the nature of interaction between the gas molecules and nanotubes. SWCNTs have been found to detect presence of $NH_3$ and/or $NO_3$, based on the charge transfer between these gases and SWCNTs. Our early tests indicated that pristine SWNTs do not respond at all when exposed to some industrial chemicals, such as chlorine and hydrogen chloride. It is important to get some observable response before one can do signal processing or pattern recognition for selective identification.

Carbon nanotubes coated with different polymers, such as polyethylene chlorosulfonated, hydroxypropyl cellulose, polystyrene, polyvinylalcohol, etc. used in commercial polymer based chemical sensors available for organic vapor detection, can provide specific interactions with a chemical species of interest. As this chemical treatment aims to provide a specific interaction between the carbon nanotube matrix and specific gas molecules, the treatment can improve the selectivity while maintaining the high sensitivity expected of a nanosensor.

Figure 2:
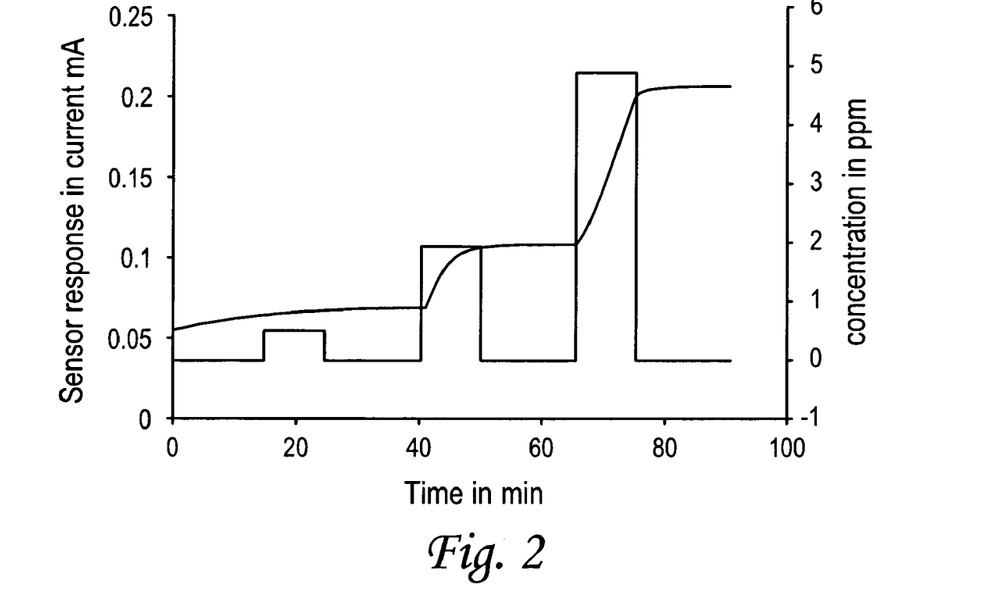
FIGS. 2 and 3 graphically illustrate sensor response (electrical current) versus concentration (C) for $Cl_2$ detection and for HCl detection, using SWCNTs coated with chlorosulfonated polyethylene and hydroxypropyl cellulose, respectively.

Several polymer-coated carbon nanotube sensors have been tested for different toxic gases, such as chlorine and hydrogen chloride; for comparison, other gases, including oxides of nitrogen ($NO_p$; p=1-3), ammonia ($NH_3$), benzene, nitrotoulene and acetone, have also been tested. FIG. 2 shows the room temperature sensor response for SWCNTs coated with chlorosulfonated polyethylene, for $Cl_2$ concentration pulses of 1, 2 and 5 ppm as shown by the sample pulses. At 1 ppm of $Cl_2$, no response is observed, but significant response is seen at 2 ppm and above. The signal strength increases at higher concentrations. Such concentration-dependent signal response is a desirable attribute. By contrast, many state of the art sensors provide a flat signal regardless of the concentration. The sensor results shown in FIG. 2 are consistently reproducible. However, the sensor recovery time is currently an issue, as is implicit in the times required (≈10 min) for reaction to change of concentration. From our previous work with $NO_p$ sensing, it is known that UV illumination of the SWNTs helps to drive out the adsorbents rapidly, thus accelerating recovery when the source of the test sample is removed.

Figure 3:
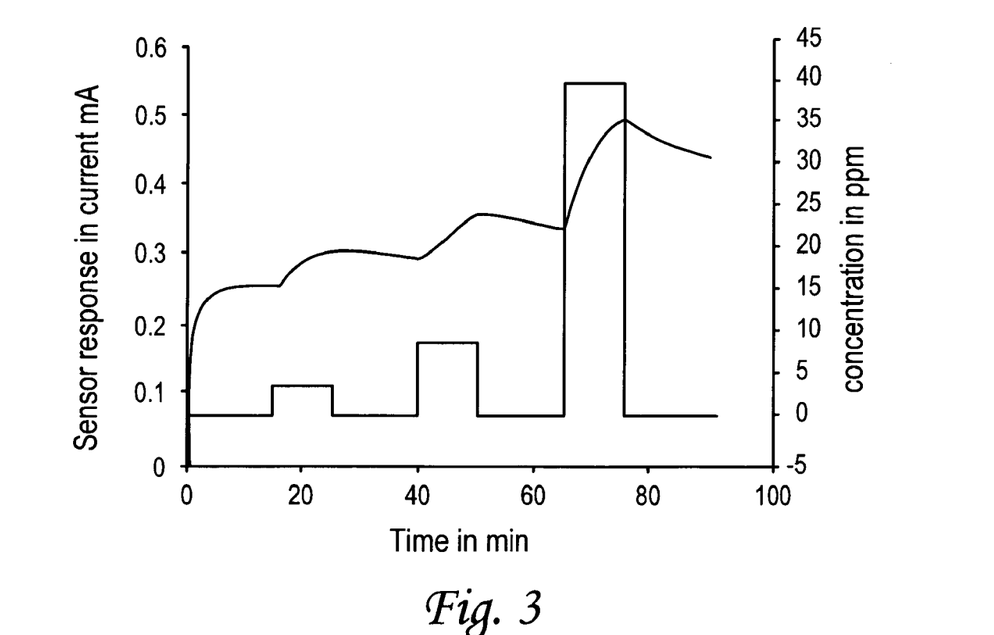

Sensors with SWCNTs coated with hydroxypropyl cellulose have been tested for HCl detection. FIG. 3 shows the sensor response for HCl concentration pulses of 5, 10 and 40 ppm. This sensor provides an observable response signal with 5 ppm HCl present, with reasonable recovery times similar to those in FIG. 2. Again, the (equilibrium) signal increases with the concentration of the analyte, and the sensor results are highly reproducible. Although the response and recovery times of this sensor for HCl are improved relative to the results for chlorine, UV illumination and heating may be used here as well for further improved performance.

Figure 4:
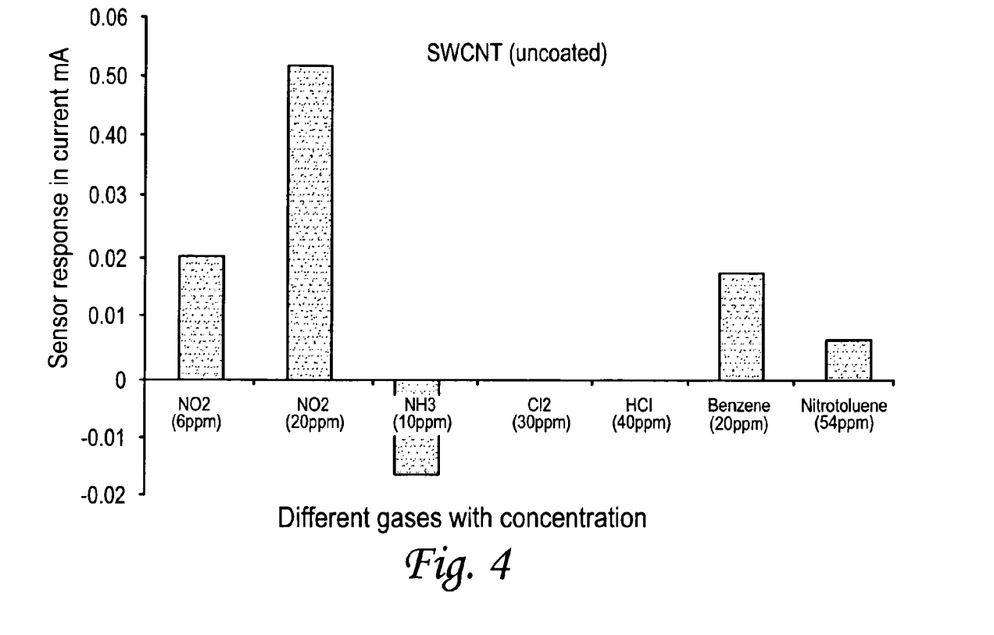
FIG. 4 compares relative response of uncoated SWCNTs for presence of $NO_2$, $NH_3$, benzene, nitrotoluene, $Cl_2$ and HCl.

A comparison experiment was conducted on sensors using pure, uncoated SWCNTs exposed to different gas and vapor analytes, with results shown in FIG. 4. The pure or uncoated SWCNT sensors showed no observable response when exposed to $Cl_2$ or to HCl, but displayed positive response signals, varying with concentration, for $NO_p$, nitrotoulene, and benzene, and showed a negative response signal (opposite polarity) for $NH_3$. Thus, the SWCNT sensor has some low level of discriminating power by itself to some, but not all, gases and vapors. It is clear from FIG. 4 that SWCNTs sensors are sensitive to $NO_p$, nitrotoulene, benzene and $NH_3$, as demonstrated previously. The opposite polarities of sensor response for $NO_p$ and for $NH_3$ is believed to be due to the electron-acceptance and electron-donation characters of these gases. In relative terms, SWCNT sensors have lower sensitivity to benzene and to nitrotoluene vapors than to $NO_p$.

Figure 5:
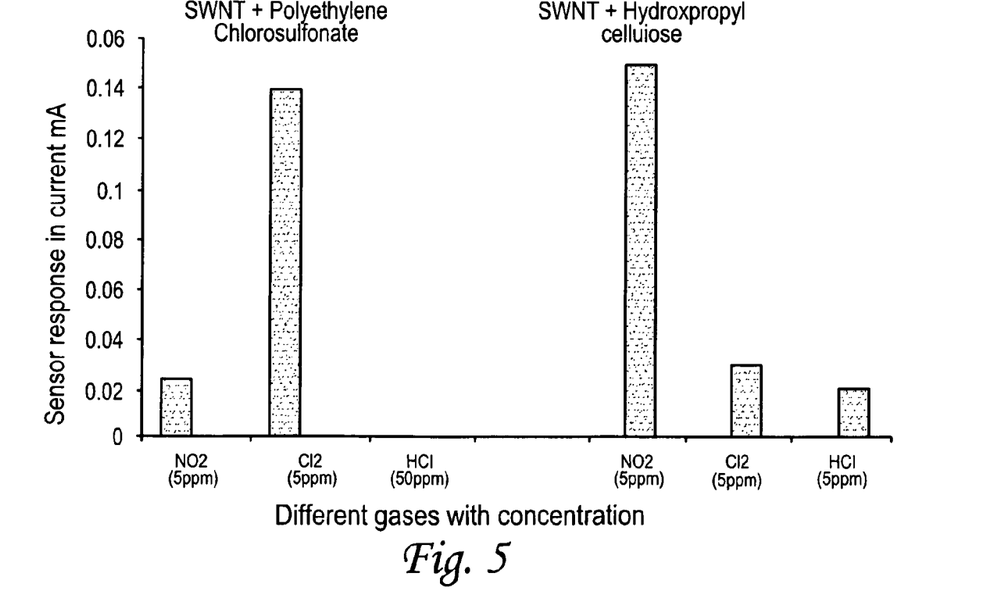
FIG. 5 compares relative response of SWCNTs coated with chlorosulfonated polyethylene or with hydroxypropyl cellulose for presence of $NO_2$, $Cl_2$ and HCl.

A similar comparison experiment was carried out on the polymer-coated SWCNT sensors exposed to different analytes, with results shown in FIG. 5. It is clear that addition of chlorosulfonated polyethylene coating to SWCNTs increases the sensitivity dramatically with a high level signal to 5 ppm $Cl_2$ compared to the pure SWCNT sensor, which shows no observable response even at 50 ppm of $Cl_2$ concentration. Although there is a signal for $NO_p$ from a chlorosulfonated polyethylene-coated SWCNT sensor, the sensing signal ratio of $Cl_2$ to $NO_p$ is much larger than 1. Therefore, this sensor can be used in a sensor array to give a distinct response signal for $Cl_2$ (and, similarly, for HCl) for discrimination.

These studies also show that both pure SWCNTs and chlorosulfonated polyethylene-coated SWCNTs do not respond to 100 ppm concentration of HCl gas in nitrogen. Higher concentrations of HCl were not tested as these high levels are not of interest for a nanosensor. In contrast, hydroxypropyl cellulose-coated SWCNTs respond to presence of HCl, but this sensor is also sensitive to $NO_p$. Presence of the OH groups in the polymer coating may be responsible for the response signal differences in interaction with acidic gases. Because this sensor gives a significant response to HCl that other SWCNT sensors do not, the sensor can be used in a sensor array to provide a chemical signature that differentiates the HCl gas from other chemicals.

We have demonstrated a simple nano-chemical sensor using polymer-coated SWCNTs as the sensing medium. Because pristine (uncoated or unmodified) nanotubes do not respond observably to some chemicals of interest, it is important to explore coating or doping techniques to promote observable responses so that a broad application coverage can be ensured. We have found that the polymer coating enables selective sensing of chlorine and hydrochloric acid vapor at a sensitivity level of 5 ppm and above. It is important to recognize that coating or doping alone is unlikely to provide absolute discrimination. As with most sensors (of any size or exploiting any property change), pattern recognition techniques would be a valuable and necessary complement to provide discrimination. In that regard, the use of sensor arrays with multiple elements is an effective approach to chemical sensing, wherein the data from multiple sensors can be routed to a signal processing chip, integrated into the system, for data fusion and analysis. Advanced signal processing and pattern recognition techniques can be used to confirm (or refute) the assumed presence of a given species, in addition to the help from the selective coatings. Multiple sensing element arrays offer additional operational freedom when sensor recovery is slow and is a rate limiting process. Under such circumstances, a sensor would always be available while other sensors are in recovery mode.

Figure 6:
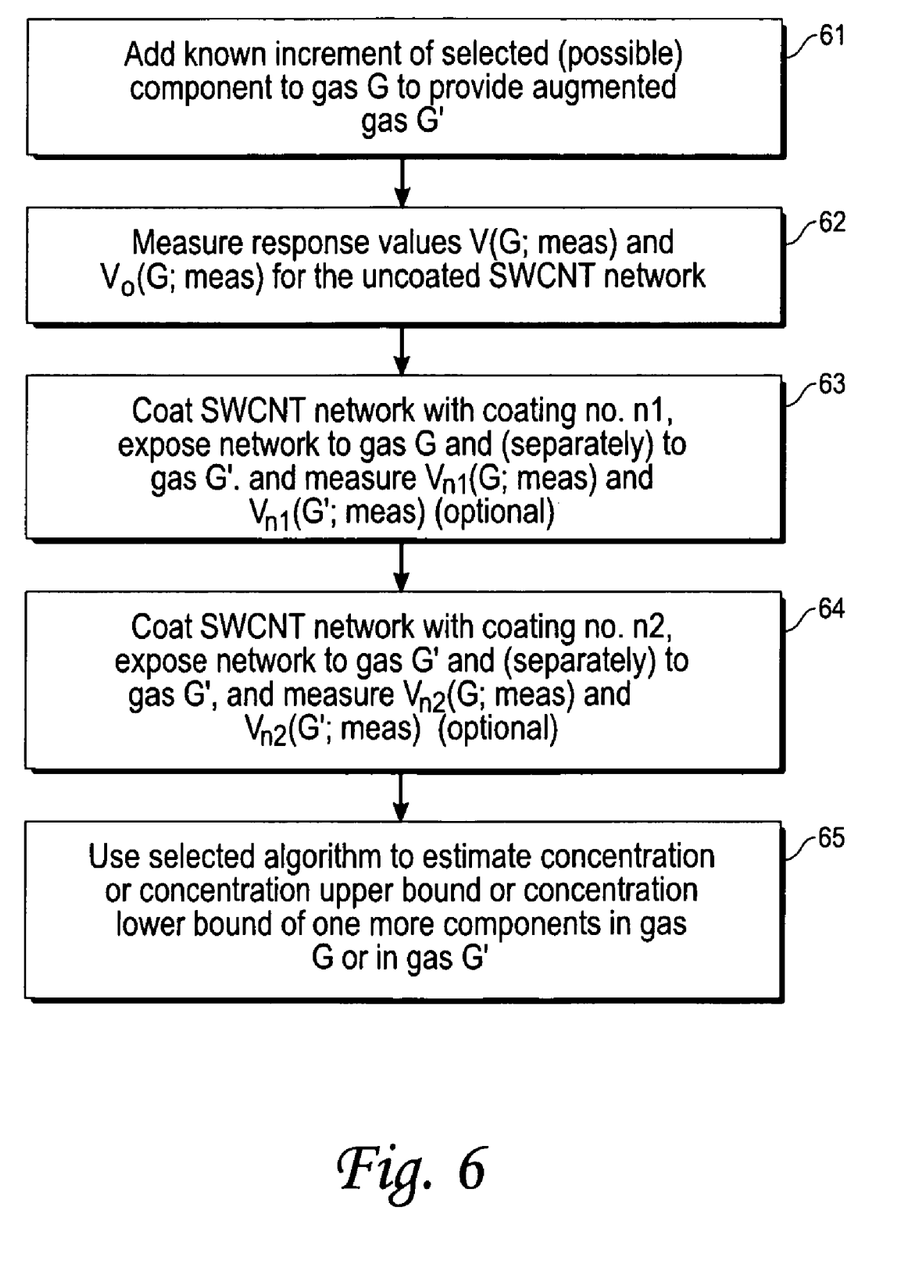
FIG. 6 is a flow chart for practicing the invention using one or more selected coatings (e.g., chlorosulfonated polyethylene or hydroxypropyl cellulose).

Using the results shown in FIG. 5, a procedure, shown as a flow chart in FIG. 6, can be implemented to detect presence of one, two or more target molecules, such as halogens, $F_2$ and/or $Cl_2$, or of one or more hydrogenated halogens, such as HCl or HBr, in an unknown gas G (which may contain $NO_p$, $NH_3$ and one or more of the target gas molecules). In step 61, a known increment of a selected (possible) component of the gas G (reference component, such as $NO_p$ or $NH_3$, or target component, such as $Cl_2$ or HCl) is added to and mixed with a portion of the gas G to provide an augmented gas G'. In step 62, response values, $V_0$(G;meas) and $V_0$(G';meas), are measured for the uncoated SWCNT network In step 63, the SWCNT network is coated with a selected coating no. n1 (e.g., chlorosulfonated polyethylene, hydroxypropyl, polystyrene, polyvinylalcohol or another suitable (first) coating), is exposed to the gas G and (separately) to the gas G', and the corresponding response values $V_{n1}$(G;meas) and $V_{n1}$(G'; meas) are measured or otherwise provided. In step 64, the SWCNT network is recycled and coated (instead) with a different selected coating no. n2 (e.g., hydroxypropyl cellulose or another suitable (second) coating), is exposed to the gas G and (separately) to the gas G', and the corresponding response values, $V_{n2}$(G;meas) and $V_{n2}$(G';meas) are measured or otherwise provided. In step 65, the system uses a selected algorithm to estimate the concentration (e.g., in ppb) or concentration upper bound or concentration lower bound of one or more of the components believed to be present in the gas G (or in the gas G'). Two suitable algorithms for determination of gas component concentration is disclosed in a flow chart in FIGS. 7 and 8, discussed in Appendices 1 and 2, respectively.

It is assumed initially in Appendix 1 that (i) the response value difference varies linearly with concentration difference of a single constituent that is present and (ii) the response value difference, in the presence of two or more gas constituents in the gas G, is the sum of the response value differences of the single constituent gases. Linear response coefficients $a_{ij}$ for the response value differences are assumed to be determined experimentally or otherwise provided. As an example, assume that one reference gas (e.g., $NO_p$ or $NH_3$) plus first and second target gases (e.g., $Cl_2$ and HCl), are suspected to be present in the gas G. Estimates cm0 of each of the concentration values $c_{m0}$ for the initial (unaugmented) gas G are obtained from inversion of an M×M matrix equation relating these concentration values to response value differences for N coatings, where M ($\geq 2$) is the number of gas components (reference and target) believed to be present and N ($\geq 1$) is the number of coatings (or dopings) used for the measurements.

The approach discussed in Appendix 1 allows separate weights, $w_n$ and $w'_n$, to be assigned to the measurements of the initial gas and augmented gas. Preferably, at least two of the weight values in Eq. (3) are positive (e.g., ($w_1$, $w_2$) or ($w'_1$, $w'_2$) or ($w_1$, $w'_2$) or ($w'_1$, $w_2$)) for the example with N=2, and the relative sizes of the non-zero weights reflect the relative importance of the response measurements. If, as is likely, the four response measurements are believed to be equally important, one can choose $w_1=w_2=w'_1=w'_2=1$. One can ignore one or two of the four measurements, in which event the corresponding weight value(s) is set equal to 0.

The response coefficients $a_{ij}$ used in Eqs. (1) and (2) are not necessarily positive. For example, the response coefficient $a_{ij}$ for the gas constituent $NO_2$ is positive for several of the SWCNT coatings used, while the response coefficient $a_{ij}$ for $NH_3$ is observed to be negative for some of these coatings.

Figure 8:
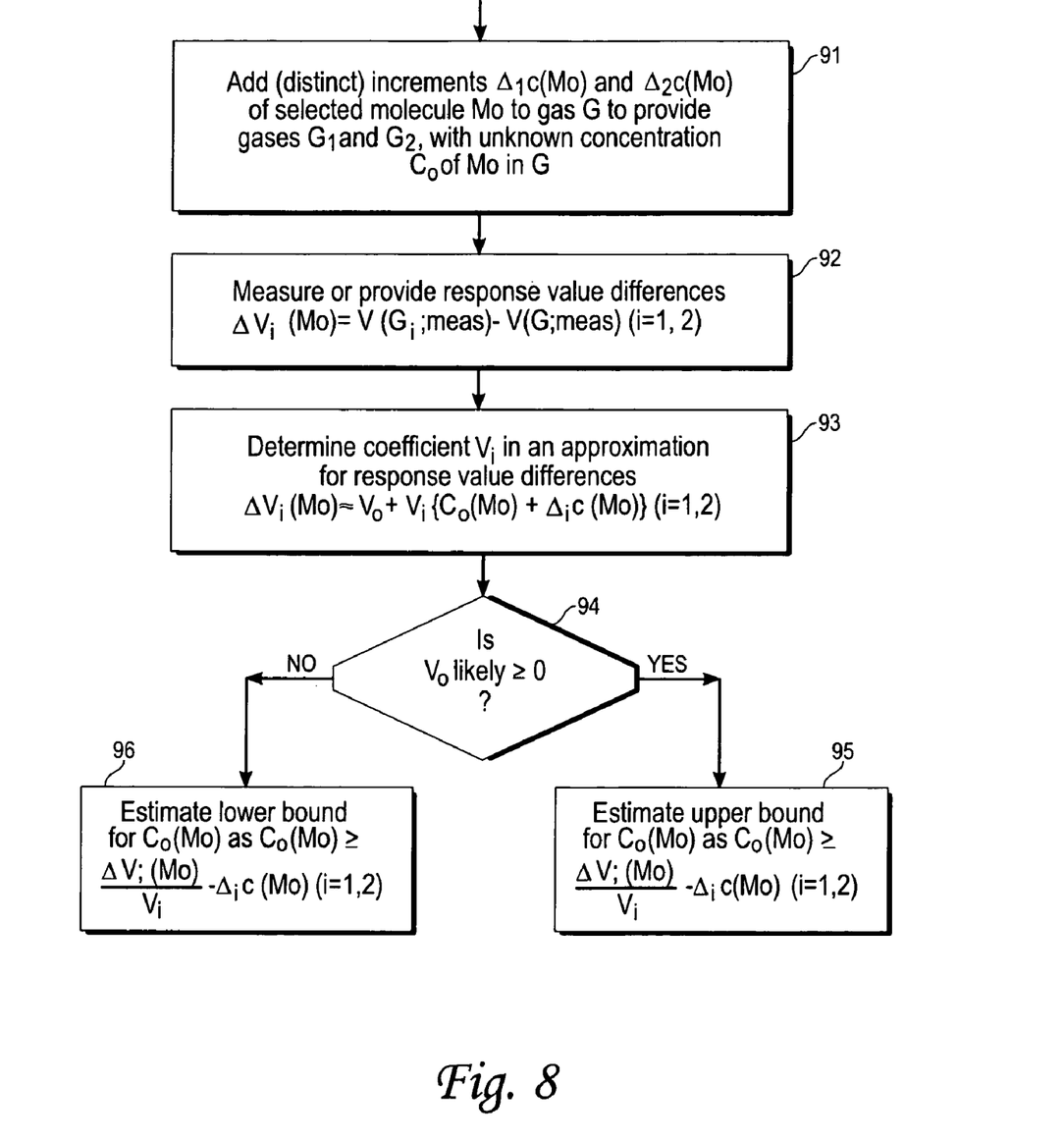

Appendix 2, and the corresponding flow chart in FIG. 8, discuss an approach for estimating an upper bound, or a lower bound, of a concentration value of a selected molecule (e.g., $NO_x$ or $NH_3$ or $Cl_2$ or HCl), again assuming that a response value difference varies linearly with a concentration value difference of the selected molecule. This bound is computed separately for each selected molecule. Appendices 1 and 2 apply to coated or doped CNT networks.

Figure 9:
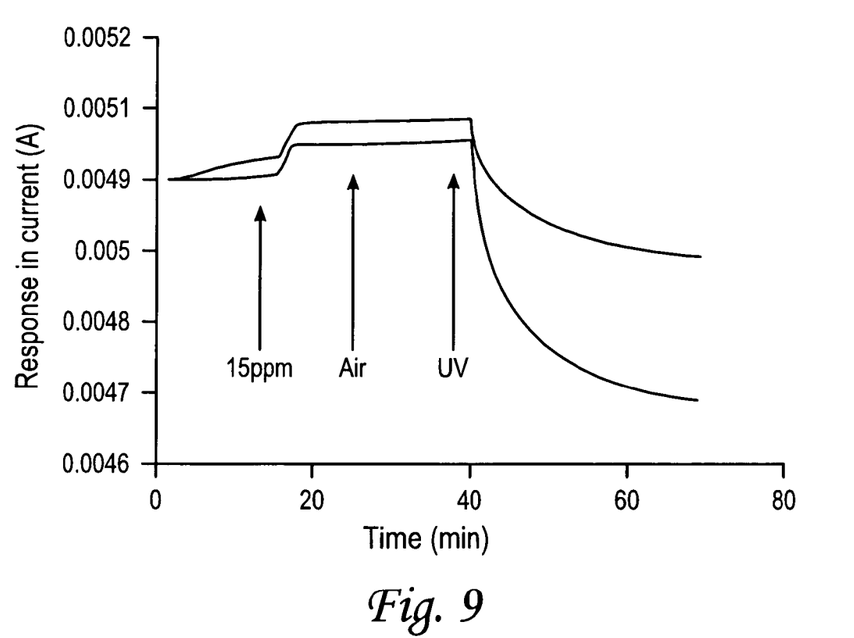
FIG. 9 graphically illustrates recovery time of a measured electrical parameter (here, current) to presence and absence of ultraviolet light.

Exposure of the coated SWCNT network to ultraviolet light can reduce the recovery time (normally ten hours or more) required to return the network to a substantially uncoated condition, by promoting accelerated detachment of the coating material from the SWCNT network. FIG. 9 graphically illustrates measured response versus time with ultraviolet light absent (sensor 1) and absent (sensor 2), indicating the improvement in recovery time where ultraviolet light is applied to lower the energy barrier to desorption of the adsorbed gas from the SWCNT network.

For some relatively small molecules, such as methane ($CH_4$), other hydrocarbons, and oxides of carbon ($CO_x$; x=1, 2), an SWCNT network, doped with a transition element ("TE",) such as Pd, Pt, Rh, Ir, Ru, Os and Au, can be used to detect presence of these molecules by detecting a change in an electrical parameter (conductance, resistance, current or voltage difference) or response value associated with a path defined by an SWCNT network that extends between two electrodes having a controllable voltage difference or current. Some molecules, including nitrotoluene and phenol, are relatively strong electron donators and/or electron acceptors, and these molecules' presence can be readily detected using "bare" or unmodified SWCNTs. Other molecules, including but not limited to methane, hydrocarbons and carbon oxides, manifest little or no electron donor or electron acceptor action so that monitoring an electric parameter value V of an unmodified or "bare" SWCNT network will, by itself, not indicate presence or absence of these molecules.

Where $CH_4$ is adsorbed in a SWCNT/Pd matrix, the combination forms a weakly bound complex, such as $Pd^\delta(CH_4)^{-\partial}$, where $\partial$ is a relatively small positive number that need not be an integer. Methane, hydrocarbons and carbon oxides are "greenhouse" gases and require detection capabilities in the ppb-ppm range to have much utility in environmental monitoring. The sensing platform is similar to that illustrated in FIGS. 1A/1B, where the SWCNT/TE compound serves as a current or voltage modifier whose electrical parameter value V changes when molecules of a selected target chemical, such as $CH_4$ or $C_mH_n$ or $CO_x$, are adsorbed on the SWCNT/TE compound, and the value V is monotonically increasing (not necessarily linearly) with increase in the amount of the target chemical present. This approach for detecting presence of a target molecule is often at least one order of magnitude more sensitive at room temperature than is detection using catalytic beads or metal oxides, in part due to (1) nanoscale-induced charge transfer between TE-loaded nanotubes and $CH_4$ molecules and (2) a relatively large surface area per unit volume for SWCNTs, which permits enhanced adsorption of hydrocarbon molecules (e.g., $CH_4$ and $C_mH_n$).

Fabrication of a sensing platform for the SWCNT/TE network begins with sputter coating of 10 nm thick Pd onto a pile of SWCNT powder. The TE-loaded or TE-doped SWCNTs are then dispersed into distilled, deionized water (e.g., 0.1 mg of SWCNT/Pd in 10 ml of the water). This solution is then sonicated and drop deposited onto interdigitated electrode fingers to create an electrical sensor with an initial resistance in a range of about 0.2-1 kilo-Ohm. Current through the network, with a 1 Volt difference, was monitored where 6, 15, 30 and 100 ppm of $CH_4$ was present, using a gas stream flow of about 400 cc/min during exposure and during purge. Apart from preparation of the doped or loaded SWCNT network (as distinguished from coating a SWCNT network), the procedure for estimation of constituents present in a gas using a doped SWCNT network, is parallel to the procedure using a coated SWCNT network set forth in the FIG. 6 flow chart.

Vacuum pumping and exposure of the network to ultraviolet light ($\lambda$=254 nm) were used to reduce the recovery time of the SWCNT/Pd (i.e., removal of the $CH_4$) between tests (no recovery if these recovery acceleration procedures are not implemented). FIG. 9 graphically illustrates measured response versus time with ultraviolet light present, indicating the improvement in recovery time where ultraviolet light is applied to lower the energy barrier to desorption of $CH_4$ molecules from the SWCNT/Pd network.

Figure 10:
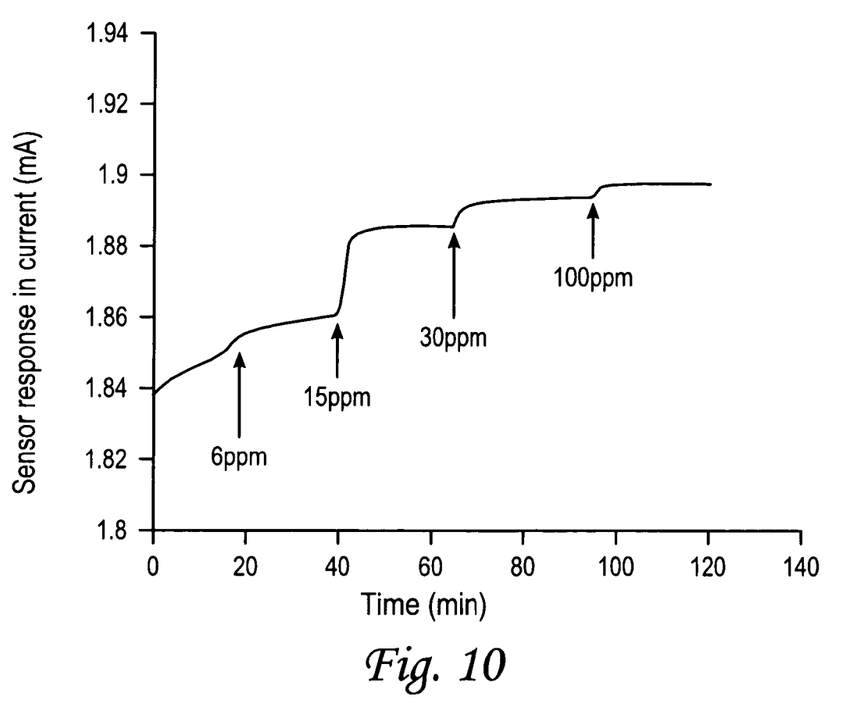
FIG. 10 graphically illustrates variation of a measured electrical parameter with time for different concentrations.

FIG. 10 graphically illustrates sensor response (current in milli-Amps) versus time for each of the $CH_4$ concentrations of 6, 20, 60 and 100 ppm, and also graphically illustrates fitting of a logarithmic function, $$V/V_0 \approx a \ln(C) - b = \ln\{C^a/\exp(b)\}, \quad (7)$$

to relative response $V/V_0$ versus $CH_4$ concentration c, for four different sensor networks. Resistance, as the electrical parameter, normally decreases with increasing concentration C of the constituent, while conductance, electrical current and voltage difference normally increase with increasing concentration c. The algorithm set forth in Appendix 1 and illustrated in Eqs. (A3)-(A6) can be applied to estimate concentration of one or more of the gases $CH_4$, $C_mH_n$ and/or $CO_x$, by replacing the concentration $C_1$ or $C_2$ or $C_3$=C by the quantity $$x = \ln\{C^a/\exp(b)\}, \quad (8)$$

where the parameters a and b will vary with the particular gas constituent of interest.

Methane, in the presence of the SWCNT network, may form a complex such as $H[Pd] \cdot CH_3$. The H atoms in $CH_4$ tend to attract electrons from Pd, which in turn can obtain electrons from the SWCNTs to facilitate formation of the complex. This behavior should also be manifest for some or all of similar transition metals, such as Pt and Ru, Rh, Ir, Os and Au. The detection lower limit for $CH_4$ at room temperature, using a Pd-doped SWCNT network, is estimated to be a few hundred ppb to a few ppm. This compares with a $CH_4$ detection lower limit of 0.5-1 percent for conventional sensors, at temperatures $T(min) \geq 450°$ C.

Figure 11:
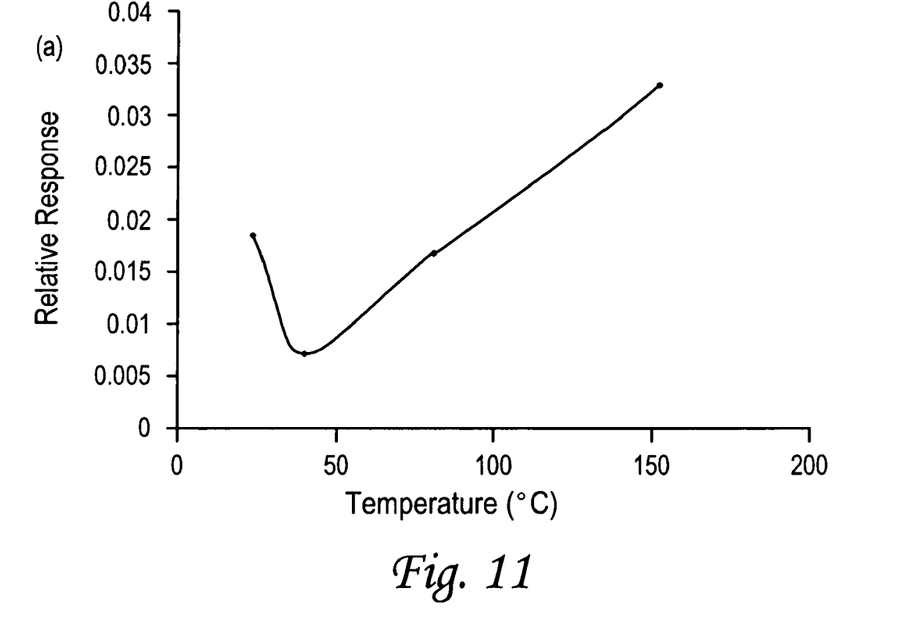
FIGS. 11 and 12 graphically illustrate behavior of a measured electrical parameter and response time with varying temperature.
Figure 12:
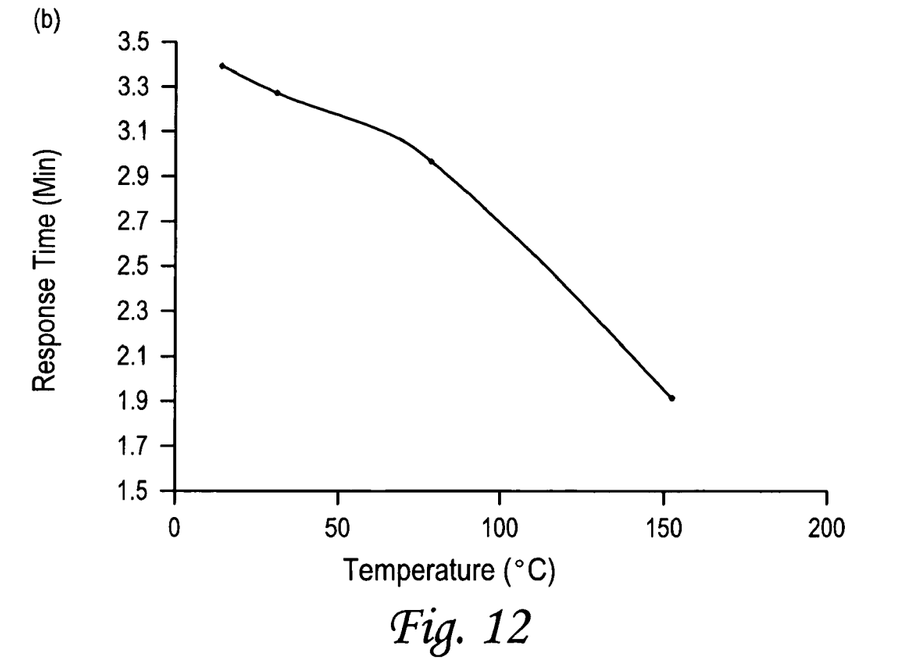

FIGS. 11 and 12 graphically illustrate the effects of varying temperature upon relative response $V/V_0$ and upon response time, respectively. The relative response in FIG. 11 appears to reach a relative minimum at a temperature $T=T(min) \approx 40°$ C. and to increase monotonically as $|T-T(min)|$ increases. At room temperature, $T \approx 20°$ C., the relative response is approximately three times the relative response at $T=T(min)$. The response time (required at approximate equilibration of the response after exposure to a gas containing the target molecule) decreases monotonically with increasing temperature T.

The SWCNT/TE sensor, with TE=Pd, has been tested at 15 ppm and 30 ppm concentrations of $CH_4$ at gas temperatures of $T=40°$ C., $80°$ C. and $150°$ C. The response parameter value (e.g., conductance or current) increases with increasing temperature, perhaps due to an enhanced catalytic effect of SWCNT/Pd binding with increasing temperature.

Experimental results for other hydrocarbons, for $CO_x$, for ketones and for aldehydes are qualitatively similar to those for $CH_4$.

Appendix 1

Estimation of Concentration of a Gas Component

Figure 7:
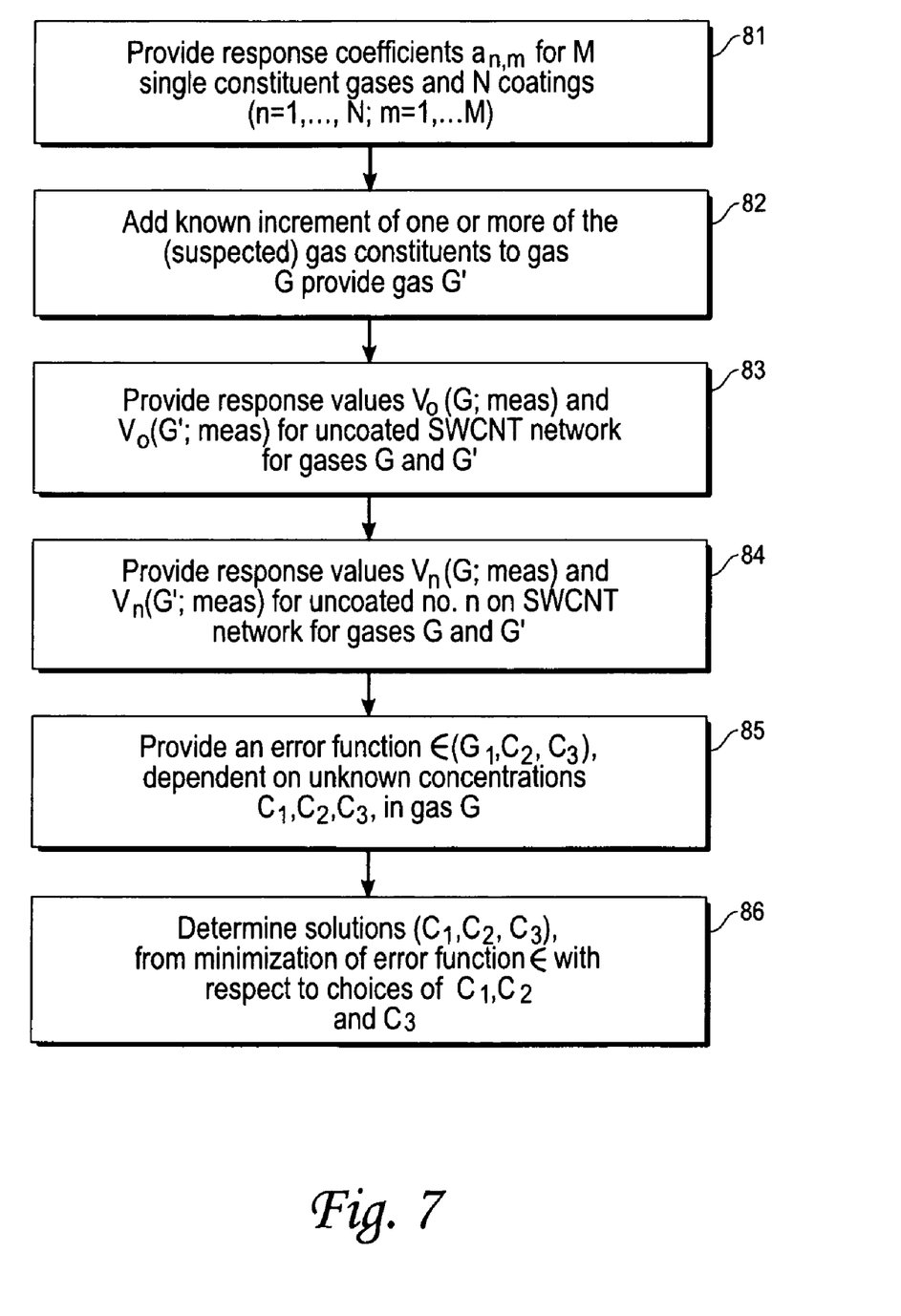
FIGS. 7 and 8 are flow charts of algorithms for estimation of concentrations of gas components and for determination of presence of a particular gas component, where a coated or doped SWCNT network is used.

FIG. 7 is a flow chart of a procedure for estimating concentration of a gas component that is suspected to be present. This approach requires knowledge of certain response coefficients relating change of a response value to increase or decrease in concentration of a particular gas component. In step 81, response coefficients $a_{n,m}$ (n=1, ..., N; m=1, 2, ..., M) are estimated or otherwise provided for M single constituent gases (numbered m=1, ..., M; $M \geq 2$), such as $NO_2$, $Cl_2$ and HCl (or for any other three gases of interest), in the presence of SWCNTs individually coated with each of N selected coatings (numbered n=1, ..., N; $N \geq 1$), for example, with chlorosulfonated polyethylene (n=1) and (separately) with hydroxypropyl cellulose (n=2):

SWCNT coated with coating number n:

$$V_n(G;meas) - V_0(G;meas) = a_{n,1} \cdot C_{NO2} + a_{n,2} \cdot C_{Cl2} + a_{n,3} \cdot C_{HCl},$$ (A1)

where, for example, $C_{NO2}$ represents the concentration (e.g., expressed in ppm or in ppb). The set of response coefficients $\{a_{n,m}\}_m$ for different coatings, n=n1 and for n=n2 ($\neq$n1), will differ from each other, but each set is determined or estimated by measurement of the response value difference, $V_n(G;meas) - V_0(G;meas)$, of coated (n) versus uncoated (n=0), for each of the three (or, more generally, M) single constituent gases present in a known concentration. For a single constituent gas $NO_2$ and no coating (n=0), for example, $a_{0,1} = 0.034 \pm 0.002$.

In step 82, a known increment of one (or more) of the (suspected) constituent (e.g., $NO_4$ or $Cl_2$ or HCl), is added to the gas unknown gas G to provide a gas G'. In step 83, the response values, $V_0(G;meas)$ and $V_0(G';meas)$, for the uncoated SWCNT network (n=0), in the presence of the gases G and G', are measured or otherwise provided. In step 84, the response values, $V_n(G;meas)$ and $V_n(G';meas)$, for the SWCNT network coated with the (single) coating number n, in the presence of the gases G and G', respectively, are measured or otherwise provided.

In step 85, an error function $\epsilon$, defined by $$2\epsilon(x,y,z) = \Sigma_n w_n \cdot \{V_n(G;meas) - V_0(G;meas) - a_{n,1}C_1 - a_{n,2}C_2 + a_{n,3}C_3\}^2 + \Sigma_n w'_n \cdot \{V_n(G';meas) - V_0(G';meas) - a_{n,1}(C_1 + \Delta C_1) - a_{n,2}C_2 + a_{n,3}C_3\}^2,$$ (A2)

is provided, where $C_1$, $C_2$ and $C_3$ refer to the concentrations of the reference molecule, the first gas molecule and the second gas molecule, $\Delta C_1$ is a known concentration increment of a selected one ($C_1$) of the reference molecule, the first gas molecule or the second gas molecule, added to the gas G to provide the gas G', and $w_n$ and $w'_n$ are selected non-negative weight values. The two sums in Eq. (A2) represent the contributions of the initial composition and the augmented composition, respectively. These sums over n may include one, two, three or more coatings for which the response coefficients are known. In this example, n=1, 2.

The error function $\epsilon(C_1, C_2, C_3)$ is to be minimized with respect to choices of the concentration values $C_1$, $C_2$ and $C_3$. Differentiating $\epsilon$ with respect to each of the variables $c_1$, $c_2$ and $c_3$, in step 86, one obtains three coupled linear equations in these variables:

$$\{(w_1 + w'_1)a_{1,1}^2 + (w_2 + w'_2)a_{2,1}^2\}C_1 + \\ \{(w_1 + w'_1)a_{1,1}a_{1,2} + (w2 + w'2)a_{2,1}a_{2,2}\}C_2 + \\ \{(w_1 + w'_1)a_{1,1}a_{1,3} + (w_2 + w'_2)a_{2,1}a_{2,3}\}C_3 = \\ \{w_1 V_1(G; meas) + w'_1(V_1(G'; meas) - a_{1,1}\Delta C_1)\}a_{1,1},$$ (A3)

$$\{(w_1 + w'_1)a_{1,1}a_{1,2} + (w_2 + w'_2)a_{2,1}a_{2,2}\}C_1 + \\ \{(w_1 + w'_1)a_{1,2}^2 + (w_2 + w'_2)a_{2,2}^2\}C_2 + \\ \{(w_1 + w'_1)a_{1,3}a_{1,2} + (w_2 + w'_2)a_{2,3}a_{2,2}\}C_3 = \\ \{w_1 V_1(G; meas) + w'_1(V_1(G'; meas) - a_{1,1}\Delta C_1)\}a_{1,2} + \\ \{w_2 V_2(G; meas) + w'_2(V_2(G'; meas) - a_{2,1}\Delta C_1)\}a_{2,2}$$ (A4)

$$\{(w_1 + w'_1)a_{1,1}a_{1,3} + (w_2 + w'_2)a_{2,1}a_{2,3}\}C_1 + \\ \{(w_1 + w'_1)a_{1,2}a_{1,3} + (w_2 + w'_2)a_{2,1}a_{2,2}\}C_2 + \\ \{(w_1 + w'_1)a_{1,3}^2 + (w_2 + w'_2)a_{2,3}^2\}C_3 = \\ \{w_1 V_1(G; meas) + w'_1(V_1(G'; meas) - a_{1,1}\Delta C_1)\}a_{1,3} + \\ \{w_2 V_2(G; meas) + w'_2(V_2(G'; meas) - a_{2,1}\Delta C_1)\}a_{2,3}.$$ (A5)

In step 86, Eqs. (A#)-(A5) in the unknowns $C_1$, $C_2$ and $C_3$ are determined, using standard matrix inversion techniques, after verification that a 3×3 (more generally, M×M) coefficient matrix for the vector $[C_1 \ C_2 \ C_3]^{tr}$ has a non-zero determinant. These solutions, x(G), y(G) and z(G), provide estimates of the concentration values of the corresponding chemicals in the gas G (or in the gas G') in step 66 of FIG. 6.

Preferably, at least two of the weight values in Eq. (A2) are positive (e.g., $(w_1, w_2)$ or $(w'_1, w'_2)$ or $(w_1, w'_2)$ or $(w'_1, w_2)$), and the relative sizes of the non-zero weights reflect the relative importance of the response measurements. If, as is likely, the four response measurements are believed to be equally important, one can choose $w_1 = w_2 = w'_1 = w'_2 = 1$. One can ignore one or two of the four measurements, in which event the corresponding weight value(s) is set equal to 0.

The response coefficients $a_{n,m}$ used in Eqs. (1) and (2) are not necessarily positive. For example, the response coefficient $a_{ij}$ for the gas constituent $NO_2$ is positive for several of the SWCNT coatings used, while the response coefficient $a_{ij}$ for $NH_3$ is observed to be negative for some of these coatings.

More generally, where M reference gas components (numbered m=1, ..., M1) and target gas components (numbered m=M1+1, ..., M1+M2=M) with unknown concentrations are believed to be present and N coatings (numbered n=1, ..., N), the error function $\epsilon$ (analogous to Eq. (A2)) is defined by $$2\epsilon(C_1, \ldots, C_M) = \Sigma_n w_n \cdot \{V_n(G;\text{meas}) - V_0(G;\text{meas}) - \Sigma_m a_{n,m} C_m\}^2 + \Sigma_n w'_n \cdot \{V_n(G';\text{meas}) - V_0(G';\text{meas}) - \Sigma_m a_{n,1}(C_m + \Delta C_m)\}^2, \quad (A6)$$

where one, or more then one, concentration value $C_m$ is augmented by a known amount $\Delta C_m$. The error function $\epsilon$ is minimized by differentiation with respect to each of the unknown concentration values $C_m$. This yields M coupled equations $$\sum_n w_n \cdot \left\{V_n(G; meas) - V_0(G; meas) - \sum_m a_{n,m} C_{m0}\right\} a_{n,m0} + \quad (A7)$$

$$\sum_n w'_n \cdot \left\{V_n(G'; meas) - V_0(G'; meas) - \sum_m a_{n,m}(C_{m0} + \Delta C_{m0})\right\}$$

$$a_{n,m0} = 0,$$

for index values m0=1, 2, ..., M. These can be restated in a matrix format as $$\sum_n (w_n + w'_n) \left\{\sum_m a_{n,m} C_{m0}\right\} a_{n,m} = \quad (A8)$$

$$\sum_n w_n \cdot \{V_n(G; meas) - V_0(G; meas)\} +$$

$$\sum_n w'_n \cdot \left\{\sum_m a_{n,m} \Delta C_{m0}\right\} a_{n,m0} + \sum_n w'_n \cdot \{V_n(G'; meas)\}.$$

After verifying that the determinant of the M×M matrix of coefficients for the quantities $C_{m0}$ in Eq. (A8) is non-zero, this M×M matrix can be inverted to determine estimates for the concentration values $C_{m0}$ (m0=1, ..., M). These concentration value estimates will depend, in part, upon the relative values chosen for the weight values $w_n$ and $w'_n$ for the coatings. Where one or more of the reference molecule concentration values $C_{m0}$ (m0=1, ..., M1) are known in advance, the estimates for these reference concentration values can be compared with the corresponding known values to evaluate the likely accuracy of the remaining estimated values.

The approach set forth in this Appendix 1 can also be used to estimate an initial concentration value $C_{m0}$ where the CNT network is doped or otherwise loaded, rather than being coated.

Appendix 2

Determination of Bound on Gas Component Concentration

A second algorithm does not require provision of a large number of response coefficients $a_{ij}$ but only seeks to determine if a particular target molecule is present in at least a selected concentration. For a selected coating, such as chlorosulfonated polyethylene or hydroxypropyl cellulose, on the CNT, a measurement of the response value difference $\Delta V = V$ (coated)−V(uncoated) is taken for modified gases, G'(1) and G'(2), where each of two distinct supplemental concentration values, $\Delta_1 C(m0)$ and $\Delta_2 C(m0)$, respectively, for a selected molecule no. m0 (e.g., $NO_x$ or $Cl_2$ or HCl) is added to the original gas G. The concentration value $C_0(m0)$ of the selected molecule present in the original gas G is unknown, and the configuration of the CNT network is unknown. It is assumed that the response value difference $\Delta V$ increases approximately linearly with the concentration difference $\Delta C(m0)$ of the selected molecule so that $$\Delta V_1(m0) = v_0 + v_1 \cdot (C_0(m0) + \Delta_1 C(m0)), \quad (B1)$$

$$\Delta V_2(m0) = v_0 + v_1 \cdot (c_0(m0) + \Delta_2 C(m0)). \quad (B2)$$

A molecule m0 should be chosen for which $|\Delta_2 C(m0) - \Delta_1 C(m0)|$ is at least equal to a selected positive threshold. The quantities $v_0$, $v_1$ and $c_0(m0)$ are then related by the equations $$v_1 = (\Delta V_2(m0) - \Delta V_1(m0))/\{\Delta_2 C(m0) - \Delta_1 C(m0)\}, \quad (B3)$$

$$v_0 + v_1 \cdot C_0(m0) = \quad (B4)$$
$$\Delta V_1(m0) - v_1 \cdot \Delta_1 C(m0) = \Delta V_2(m0) - v_1 \cdot \Delta_2 C(m0),$$

and $v_0$ and $v_1$ are determined, in part, by the CNT network configuration (assumed fixed and reusable) that is present. Where, as is likely, $v_0 \geq 0$, one infers that the initial concentration value $C_0(m0)$ for the molecule Mo is limited by $$C_0(m0) = \{\Delta V_1(m0) - v0\}/v_1 - \Delta_1 C(m0) \leq \{\Delta V_1(m0)/v_1\} - \Delta_1 C(m0) \quad (B5-1)$$

$$C_0(m0) = \{\Delta V_2(m0) - v0\}/v_1 - \Delta_2 C(m0) \leq \{\Delta V_2(m0)/v_1\} - \Delta_2 C(m0) \quad (B5-2)$$

Equation (B5) provides an upper bound for the quantity $C_0(m0)$. Where it is known that the coefficient $v_0$ is non-positive, Eq. (B5) can be inverted to provide lower bounds for the concentration:

$$C_0(m0) = \{\Delta V_1(m0) - v0\}/v_1 - \Delta_1 C(m0) \geq \{\Delta V_1(m0)/v_1\} - \Delta_1 C(m0) \quad (B6-1)$$

or $$C_0(m0) = \{\Delta V_2(m0) - v0\}/v_1 - \Delta_2 C(m0) \geq \{\Delta V_2(m0)/v_1\} - \Delta_2 C(m0) \quad (B6-2)$$

This approach does not provide a direct estimate for the quantity $C_0(m0)$, only an indication of whether the molecule Mo is or is not present in a concentration of no more than the right hand quantity in Eq. (B6) or (B7). However, this approach does not require determination and use of the response coefficients $a_{ij}$ that are required for the putatively more accurate method set forth in Appendix 1. The method of Appendix 2 can be used to estimate upper (or lower) bounds for concentration values C of one, two or more selected molecules.

FIG. 8 is a flow chart of a procedure for estimating an upper bound for a concentration value $C_0(m0)$ for a selected molecule in the gas G. It is assumed that the response value difference $\Delta V$ varies approximately linearly with the concentration difference $\Delta C(m0)$ of the selected molecule. In step 91, first and second (distinct) known increments, $\Delta_1 C(m0)$ and $\Delta_1 C(m0)$, of a selected molecule Mo are added to a gas G to provide first and second augmented gases, G1 and G2. In step 92, response value differences, $$\Delta V_1(Mo) = V(G1;\text{meas}) - V(G;\text{meas}), \tag{B7}$$

$$\Delta V_2(Mo) = V(G2;\text{meas}) - V(G;\text{meas}), \tag{B8}$$

are measured or otherwise provided. In step 93, the coefficient v1 in an approximation for response value differences $$\Delta V_1(m0) = v_0 + v_1 \cdot \{C_0(m0) + \Delta_1 C(m0)\}, \tag{B1}$$

$$\Delta V_2(m0) = v_0 + v_1 \cdot \{C_0(m0) + \Delta_2 C(m0)\}, \tag{B2}$$

is determined according to $$v_1 = (\Delta V_2(m0) - \Delta V_1(m0))/\{\Delta_2 C(m0) - \Delta_1 C(m0)\}. \tag{B3}$$

In step 94, the system queries whether the coefficient $v_0$ is likely non-negative. If the answer to the query in step 94 is "yes," the system estimates an upper bound for the initial concentration value $C_0(m0)$, in step 95:

$$C_0(m0) \leq \tag{B5}$$
$$\{\Delta V_1(m0)/v_1 - \Delta_1 C(m0) = \Delta V_2(m0)/v_1 - \Delta_2 C(m0)(v_0 \geq 0).$$

If the answer to the query in step 94 is "no," the system estimates a lower bound for the initial concentration value $C_0(m0)$, in step 96:

$$C_0(Mo) \geq \tag{B6}$$
$$\{\Delta V_1(m0)/v_1 - \Delta_1 C(m0) = \Delta V_2(m0)/v_1 - \Delta_2 C(m0)(v_0 \leq 0).$$

What is claimed is:

1. A method for providing a sensor for presence of at least one of a first selected gas molecule and a second selected gas molecule, the method comprising:
   providing, in a chamber, first and second interdigitated electrodes, which are connected to at least one of (i) a voltage source having a controllable voltage difference and (ii) a controllable current source;
   providing a zeroth order electrically conducting network, numbered 0, of uncoated single wall carbon nanotubes ("SWCNTs") forming a path P0 between the first and second electrodes;
   providing N electrically conducting networks, numbered $n=1, \ldots, N$ ($N \geq 1$) of single wall carbon nanotubes ("SWCNTs") forming paths Pn ($n=1, \ldots, N$) between the first and second electrodes, where at least one SWCNT in each of the networks no. n ($n=1, \ldots, N$) is loaded with molecules of a selected chemical no. n;
   providing in the chamber a gas G that may have molecules of a gas constituent no. m present in a concentration $C_m$ ($m=1, \ldots, M$; $M \geq 1$), where at least one of the concentration values $C_m$ is unknown, allowing at least one molecule of the gas G to become absorbed on at least one of the SWCNTs in each of the paths P0 in the zeroth order network and Pn in the network number n ($n=1, \ldots, N$);
   providing an electrical parameter value ("response value") $V_0(G;\text{meas})$, associated with the path P0, of at least one of (i) electrical current, (ii) electrical conductance, (iii) voltage difference and (iv) electrical resistance associated with the path P0, when the gas G is present, and providing a corresponding response value $V_n(G;\text{meas})$, associated with the path Pn ($n=1, \ldots, N$) when the gas G is present;
   adding a known concentration increment $\Delta_1 C_{m0}$ of a gas constituent no. m0, selected from among the M constituents, to the gas G to provide an augmented gas G', allowing at least one molecule of the gas G' to become absorbed on at least one of the SWCNTs in each of the path P0 and Pn ($n=1, \ldots, N$), and providing corresponding response values $V_0(G';\text{meas})$ and $V_n(G';\text{meas})$ for the gas G';
   comparing differences, $V_n(G;\text{meas}) - V_0(G;\text{meas})$ and $V_n(G;\text{meas}) - V_0(G';\text{meas})$ ($n=1, \ldots, N$) of the response values and estimating at least one of (i) concentration and (ii) concentration upper bound and (iii) concentration lower bound for at least one of the first gas molecule and the second gas molecule present in at least one of the gas G and the gas G'
   wherein the process of estimating at least one of (i) the concentration C and (ii) the concentration upper bound and (iii) the concentration lower bound comprises:
   providing an error function $\epsilon(C_1, \ldots, C_M)$, defined by $$2\epsilon(C_1, \ldots, C_M) = \Sigma_n w_n \cdot \{V_n(G;\text{meas}) - V_0(G;\text{meas}) - \Sigma_m a_{n,m} C_m\}^2 + \Sigma_n w'_n \cdot \{V_n(G';\text{meas}) - V_0(G';\text{meas}) - a_{n,m}(C_m + \Delta C_m)\}^2,$$

where $a_{n,m}$ is a response value coefficient relating change in the response value $V_n(G;\text{meas})$ to change in the concentration $C_m$ of the constituent no. m, $\Delta C_m$ is a known concentration increment of the gas constituent no. m, added to the gas G to provide the gas G', $w_n$, and $w'_n$ are selected non-negative weight values, and at least one increment value $\Delta C_m$ is positive;
   forming M partial derivatives of the error function $2\epsilon(C_1, \ldots, C_M)$ with respect to the concentrations $C_1, \ldots, C_M$, to provide M non-homogeneous, linear equations relating the concentrations $C_1, \ldots, C_M$;
   solving the M non-homogeneous linear equations to provide values, $C_m(\min)$ for the concentrations $C_m$ as solutions of the equations; and
   associating at least one of the values $C_m(\min)$ with an estimate of the concentration of the constituent no. m in at least one of the gas G and the gas G'.

2. The method of claim 1, further comprising choosing at least one of said first gas molecule and said second gas molecule from a group consisting of $NO_x$, $NH_3$, acetone, benzene, nitrotoluene, $F_2$, $Cl_2$, $Br_2$, $I_2$, HF, HCl, HBr, HI, an alcohol, an aldehyde and a ketone.

3. The method of claim 1, further comprising choosing at least one of said first gas molecule and said second gas molecule from a group consisting of a halogen, a hydrogenated halogen, an alcohol, an aldehyde and a ketone.

4. The method of claim 3, further comprising:
   drawing said chemical no. n from the group of chemicals consisting of chlorosulfonated polyethylene, hydroxypropyl, polystyrene, and polyvinylalcohol; and
   loading said selected chemical no. n by coating said chemical no. n ($n=1, \ldots, N$) on said at least one of said SWCNTs in said path Pn.

5. The method of claim 1, further comprising choosing at least one of said first gas molecule and said second gas molecule from a group consisting of a hydrocarbon and an oxide of carbon.

6. The method of claim 5, further comprising:
   drawing said chemical no. n from the group of chemicals consisting of Pd, Pt, Rh, Ir, Ru, Os and Au; and loading said selected chemical no. n by doping said chemical no. n (n=1, ..., N) on said at least one of said SWCNTs in said path Pn.

7. The method of claim 1, further comprising:
exposing at least one of said path P0 and said path Pn (n=1, ..., N) to light having an ultraviolet component for a time interval having at least a selected time interval length $\Delta t(min)$; and
allowing at least one of said components of at least one of said gas G and said gas G' to become desorbed from said at least one SWCNT in at least one of said paths P0 and Pn (n=1, ..., N).

8. The method of claim 1, further comprising including in at least one of said electrodes in a first array having a coating of Ti and Au, having selected coating thicknesses, deposited on an exposed surface of a substrate that is substantially nonconducting electrically.

9. The method of claim 1, further comprising choosing said weight numbers $w_n$ and $w'_n$ to be substantially equal for at least one of said integers n.

10. A method for providing a sensor for presence of at least one of a first selected gas molecule and a second selected gas molecule, the method comprising:
providing, in a chamber, first and second interdigitated electrodes, which are connected to at least one of (i) a voltage source having a controllable voltage difference and (ii) a controllable current source;
providing a zeroth order electrically conducting network, numbered 0, of uncoated single wall carbon nanotubes ("SWCNTs") forming a path P0 between the first and second electrodes;
providing N electrically conducting networks, numbered n=1, ..., N (N≧1) of single wall carbon nanotubes ("SWCNTs") forming paths Pn (n=1, ..., N) between the first and second electrodes, where at least one SWCNT in each of the networks no. n (n=1, ..., N) is loaded with molecules of a selected chemical no. n;
providing in the chamber a gas G that may have molecules of a gas constituent no. m present in a concentration $C_m$ (m=1, ..., M; M≧1), where at least one of the concentration values $C_m$ is unknown, allowing at least one molecule of the gas G to become absorbed on at least one of the SWCNTs in each of the paths P0 in the zeroth order network and Pn in the network number n (n=1, ..., N);
providing an electrical parameter value ("response value") $V_0(G;meas)$, associated with the path P0, of at least one of (i) electrical current, (ii) electrical conductance, (iii) voltage difference and (iv) electrical resistance associated with the path P0, when the gas G is present, and providing a corresponding response value $V_n(G;meas)$, associated with the path Pn (n=1, ..., N) when the gas G is present;
adding a known concentration increment $\Delta_1 C_{m0}$ of a gas constituent no. m0, selected from among the M constituents, to the gas G to provide an augmented gas G', allowing at least one molecule of the gas G' to become absorbed on at least one of the SWCNTs in each of the path P0 and Pn (n=1, ..., N), and providing corresponding response values $V_0(G';meas)$ and $V_n(G';meas)$ for the gas G';
comparing differences, $V_n(G;meas)-V_0(G;meas)$ and $V_n(G';meas)-V_0(G';meas)$ (n=1, ..., N) of the response values and estimating at least one of (i) concentration and (ii) concentration upper bound and (iii) concentration lower bound for at least one of the first gas molecule and the second gas molecule present in at least one of the gas G and the gas G';
wherein the process of estimating at least one of (i) the concentration C and (ii) the concentration upper bound and (iii) the concentration lower bound comprises:
adding a second known concentration increment $\Delta_2 C_{m0}$ of the selected gas constituent, selected from among the M constituents, to the gas G to provide a second augmented gas G", allowing at least one molecule of the gas G" to become absorbed on at least one of the SWCNTs in each of the paths P0 and Pn (n=1, ..., N), and providing corresponding response values $V_0(G";meas)$ and $V_n(G";meas)$ for the gas G";
providing response value differences, $\Delta V_n(G';G)=V_n(G';meas)-V_n(G;meas)$ and $\Delta V_n(G''';G)=V_n(G";meas)-V_n(G;meas)$;
determining a response coefficient v1 as $$v1=\{\Delta V(G";G)-\Delta V(G';G)\}/\{\Delta_2 C_{m0}-\Delta_1 C_{m0}\}; \text{ and}$$

estimating said concentration $C_{m0}$ of the selected gas constituent no. m0 in said gas G according to at least one relation $$C_{m0}=\{\Delta V(G';G)-v0\}/v1-\Delta_1 C_{m0}\}$$

and $$C_{m0}=\{\Delta V(G";G)-v0\}/v1-\Delta_2 C_{m0}\},$$

where v0 is an estimated reference value of a response value difference, $\Delta V_n(G';G)$ or $\Delta V_n(G";G)$.

11. The method of claim 10, further comprising estimating an upper bound for said concentration Cm0 according to at least one relation $$C_{m0} \leq \{\Delta V(G';G)/v1\}-\Delta_1 C_{m0}$$

and $$C_{m0} \leq \{\Delta V(G";G)/v1\}-\Delta_2 C_{m0},$$

where said estimated reference value v0 is non-negative.

12. The method of claim 10, further comprising estimating an upper bound for said concentration Cm0 according to at least one relation $$C_{m0} \geq \{\Delta V(G';G)/v1\}-\Delta_1 C_m\}$$

and $$C_{m0} \geq \{\Delta V(G";G)/v1\}-\Delta_2 C_{m0},$$

where said estimated reference value v0 is non-positive.

* * * * *